United States Patent
Dobschal et al.

(10) Patent No.: US 9,265,658 B2
(45) Date of Patent: Feb. 23, 2016

(54) CONTACT ELEMENT FOR LASER MACHINING

(75) Inventors: Hans-Jürgen Dobschal, Kleinromstedt (DE); Marco Hanft, Jena (DE); Mario Gerlach, Hohen Neuendorf (DE)

(73) Assignee: Carl Zeiss Meditec AG, Jena (DE)

( * ) Notice: Subject to any disclaimer, the term of this patent is extended or adjusted under 35 U.S.C. 154(b) by 2015 days.

(21) Appl. No.: 10/590,502

(22) PCT Filed: Jan. 25, 2005

(86) PCT No.: PCT/EP2005/000704
§ 371 (c)(1),
(2), (4) Date: Aug. 24, 2006

(87) PCT Pub. No.: WO2005/079717
PCT Pub. Date: Sep. 1, 2005

(65) Prior Publication Data
US 2007/0179478 A1 Aug. 2, 2007

(30) Foreign Application Priority Data

Feb. 25, 2004 (DE) .......................... 10 2004 009 212

(51) Int. Cl.
*B23K 26/06* (2014.01)
*B23K 26/16* (2006.01)
*B23K 26/00* (2014.01)
*A61F 9/009* (2006.01)
*A61F 9/008* (2006.01)

(52) U.S. Cl.
CPC ............. *A61F 9/009* (2013.01); *A61F 9/00825* (2013.01); *A61F 2009/00872* (2013.01)

(58) Field of Classification Search
CPC .. A61F 9/00825; A61F 9/00827; A61F 9/009
USPC ............... 219/121.75, 121.6, 121.61, 121.78, 219/121.79; 604/4, 5; 606/4, 5, 6, 9, 10, 11, 606/12, 15, 19; 359/558, 563, 569, 573, 359/237–324, 204.5, 107.7, 211.6, 217.4, 359/568
See application file for complete search history.

(56) References Cited

U.S. PATENT DOCUMENTS

| 5,296,673 | A | * | 3/1994 | Smith ....................... 219/121.68 |
| 5,336,215 | A | | 8/1994 | Hsueh et al. |
| 5,549,632 | A | | 8/1996 | Lai |
| 5,571,107 | A | | 11/1996 | Shaibani et al. |

(Continued)

FOREIGN PATENT DOCUMENTS

| EP | 1 159 986 A2 | 12/2001 |
| EP | 1 364 632 A1 | 11/2003 |

(Continued)

*Primary Examiner* — Hung D Nguyen
(74) *Attorney, Agent, or Firm* — Patterson Thuente Pedersen, P.A.

(57) ABSTRACT

An optical contact element for coupling a laser processing device to an object to be processed is described, wherein the laser processing device focuses a scanned laser beam through a surface of the object into a certain region of the object and the contact element comprises an entrance side for receiving the scanned laser radiation and an exit side imparting a defined surface curvature to the surface of the object upon contact therewith, wherein a diffractive optical element is provided on the entrance side, which element reduces the angle of incidence of the laser radiation on the surface of the object.

13 Claims, 3 Drawing Sheets

(56) References Cited

U.S. PATENT DOCUMENTS

| | | | |
|---|---|---|---|
| 5,673,096 A * | 9/1997 | Dorsel et al. | 351/211 |
| 5,715,081 A * | 2/1998 | Chastang et al. | 359/385 |
| 5,914,814 A * | 6/1999 | Ang | 359/565 |
| 5,973,781 A * | 10/1999 | Moeller et al. | 356/495 |
| 5,984,916 A | 11/1999 | Lai | |
| 6,146,375 A | 11/2000 | Juhasz et al. | |
| 6,254,595 B1 | 7/2001 | Juhasz et al. | |
| 6,342,053 B1 | 1/2002 | Berry | |
| 6,373,571 B1 | 4/2002 | Juhasz et al. | |
| 7,104,649 B2 * | 9/2006 | Otten et al. | 351/212 |
| 2001/0021844 A1 | 9/2001 | Kurtz et al. | |
| 2002/0103482 A1 | 8/2002 | Scholler et al. | |
| 2002/0105617 A1 * | 8/2002 | Norrby et al. | 351/177 |
| 2002/0167644 A1 | 11/2002 | Pollack et al. | |
| 2003/0053219 A1 * | 3/2003 | Manzi | 359/676 |
| 2003/0217995 A1 * | 11/2003 | Toyofuku et al. | 219/121.71 |

FOREIGN PATENT DOCUMENTS

| | | | | |
|---|---|---|---|---|
| JP | 2001-256672 A * | 9/2001 | | |
| WO | WO 0078242 A1 * | 12/2000 | | |
| WO | WO 03/002008 A1 | 1/2003 | | |
| WO | WO 03001272 A2 * | 1/2003 | | G02B 21/00 |

* cited by examiner

CONTACT ELEMENT FOR LASER MACHINING

FIELD OF THE INVENTION

The invention relates to an optical contact element for coupling a laser processing device to an object to be machined, wherein the laser processing device focuses a scanned laser beam through a surface of the object into a certain region of the object and the contact element comprises an entrance side for receiving the scanned laser radiation and an exit side imparting a defined surface curvature to the object upon contact therewith. The invention further relates to the advantageous use of such contact element in a laser processing device.

BACKGROUND OF THE INVENTION

In material processing by means of laser radiation, the laser beam's exactness of positioning usually determines the precision achieved in processing. If the laser beam is focused into a processing volume, exact three-dimensional positioning is required. If the object to be machined has a deformable surface, it is usually indispensable in high-precision processing to know the surface shape or to keep any deviation of the surface shape from a predefined shape as small as possible. The above-mentioned contact element serves such purposes, because it imparts a desired surface curvature to the surface of the object to be processed.

In materials having only minor linear optical absorption within the spectral range of the processing laser radiation advantage is usually taken of non-linear interactions between the laser radiation and the material, most often in the form of an optical breakthrough being generated in the focus of the laser beam. Since the processing effect thus only takes place in the laser beam focus, exact three-dimensional orientation of the focal point is indispensable. Thus, the machining of larger areas also requires an exact depth position of the focal location in addition to two-dimensional deflection of the laser beam. Due to the contact element, known optical relationships, in particular relationships of diffraction, with the object are present. In addition, the contact element also fixes the object in a defined position relative to the processing device.

A typical application of such a contact element is the ophthalmic surgery method known as fs-LASIK, wherein a laser beam is focused in the cornea to a focal point with an order of magnitude of a few micrometers. In the focus, a plasma then forms which suddenly evaporates and disrupts the surrounding tissue. This type of interaction between laser light and tissue is referred to as photodisruption. Since photodisruption ideally remains limited to a microscopically small zone of interaction, precise surgical cuts can be performed within the eye. Local separation of corneal tissue is effected. A suitable sequential arrangement of the local separation zones thus generated realizes macroscopic cuts and isolates a defined partial volume of the cornea. Removal of said partial volume then achieves a desired change in refraction of the cornea, thus enabling correction of an eyesight defect.

Exact positioning of the laser beam is indispensable to carry out the method. A randomly involuntary movement of the human eye during treatment is problematic. Mechanical fixation of the eye or optical feedback with respect to the eye movement is required in order to minimize this factor of influence. This is why the above-mentioned contact element is used having a double function: Not only does it ensure the required optical properties when passing the laser beam into the cornea, but it also fixes the eye, preferably with regard to several degrees of freedom, particularly preferably with regard to all possible degrees of freedom. Movements of the eye relative to the laser processing device are thus prevented.

U.S. Pat. No. 6,342,053 proposes to fix the eye by means of a vacuum ring. A coupling medium in front of the eye significantly reduces the difference in refractive index with respect to the cornea. The use of this coupling medium facilitates optical correction of the system. Since said medium has a refractive index of >1, the beam deflection at the boundary surface is further reduced and any aberrations generated at this surface are reduced. In case the refractive indices of the contact glass and of the cornea are identical, no boundary surface exists from a geometrical/optical point of view.

A different concept is described in U.S. Pat. No. 5,549,632. The corneal curvature is nullified by means of a plane-parallel plate or is deformed by a concave or convex surface. This is effected by pressure on the eye. The eye is fixed, and the focused laser bundle is not affected negatively by excessively oblique incidence on a boundary surface. The pressure on the cornea inevitably leads to an increase in the internal pressure of the eye. From a medical point of view, this increase bears risks. Further, "flattening" the cornea in order to achieve a planar geometry is inconvenient for the patient.

High field strengths are a prerequisite for the process of photodisruption; these are realized by small focus diameters and short laser pulses. Small focus diameters can be achieved only with great apertures. Moreover, fields of treatment having a diameter of more than 8 mm are of interest. The geometry of the cornea results in a curved image field. No systems are known to reach an aperture of more than 0.3 with such fields. Therefore, the prior art either is either limited to smaller processing fields or works with planar geometry.

It is an object of the invention to improve a coupling element or a laser processing device of the above-mentioned type such that larger processing fields are also possible without planar geometries.

SUMMARY OF THE INVENTION

This object is achieved by an optical contact element for coupling a laser processing device to an object to be processed, wherein the laser processing device focuses a scanned laser beam through a surface of the object into a certain region of the object and the contact element comprises an entrance side for receiving the scanned laser radiation and an exit side imparting a defined surface curvature to the object upon contact therewith, wherein a diffractive optical element is arranged on the entrance side so as to reduce the angle of incidence of the laser radiation on the surface of the object.

Thus, according to the invention the optical contact element comprises a diffractive optical element, the use of which makes it possible to combine a large field of application, i.e. image field in the object, onto which the scanned laser beam can be focused, with a surface curvature that does not force a considerable increase in the internal pressure of the eye in ophthalmic surgery applications. The use of an optical element having a diffractive effect is essential to the invention. The element deflects light through diffraction at grating structures. Due to the diffractive optical element, for example in the form of a grating, the desired large numerical aperture on the image side can be generated with considerably smaller angles of incidence on the contact glass. Thus, the numerical aperture of the focusing optics may be designed to be considerably smaller than without the diffractive optical element.

In addition to the more beneficial conditions for correction, the contact glass according to the invention also allows a greater focal length of the optics focusing the laser beam, because the required inclination of the beam in front of the contact glass has become smaller for the same diameter of the incident ray bundle due to the effect of the diffractive optical element. The increased focal length facilitates the accommodation of additional components, e.g. of a beam splitter, and the realization of application-related design specifications for constructional space. Nevertheless, an "abnormal" image field curvature with respect to ophthalmic surgery, i.e. an image field having a convex curvature, can be achieved in a simple manner by the diffractive optical element. If use were made only of optically refractive elements, a much greater limitation would be given with respect to the curvature of the image field if a large field diameter is required.

It goes without saying that the contact element is to be selected to suit the objective. For convex objects such as those present in ophthalmic surgery in the form of the human eye, it is advantageous to provide the contact element with a planoconcave base body whose concave surface provides the exit side and whose planar surface provides the entrance side. The diffractive optical element can be conveniently attached to the planar entrance side. However, it is possible to provide directly preceding independent components as well as forming the diffractive optical element directly on the planar entrance side.

For ophthalmic surgery, it is further convenient to provide the surface curvature such that it is substantially rotation-symmetrical to an optical axis of the laser processing device. This is also convenient for other applications, because the diffractive optical element then has rotation symmetry or point symmetry to the point of intersection of the optical axis. It is convenient for rotation-symmetrical geometries if the diffractive optical element diffracts such laser radiation towards the optical axis as is incident at a distance from the optical axis, with the angle of diffraction increasing as the distance from the optical axis increases. This design achieves the "abnormal" curvature of the image field desired for ophthalmic applications.

One possibility of providing the diffractive optical element is to provide it as a grating structure with a line number depending on the distance from the optical axis. The line number is typically at least 220 lines/mm and usually not more than 500 lines/mm.

The diffractive optical element can then be described by a phase polynomial as well as a frequency equation. For a spherical surface curvature the phase polynomial is, for example:

$$Ph(r) := \sum_{i=1}^{N} c_i \cdot r^{2 \cdot i}.$$

The parameters $c_i$ are to be adapted to the actual geometry; r designates the radial parameter, i.e. the radial distance from the center. The frequency equation for the number of lines per millimeter is given by:

$$\text{Frequency}(r) := \frac{\frac{d}{dr} Ph(r)}{l},$$

wherein l is the wavelength of synthesis.

The diffractive optical element allows dispensing with an exact adaptation of the refractive index between the material of the contact element and the object to be processed. Thus, the diffractive optical element allows more freedom in selecting the material for the contact element because effects of refraction appearing at the boundary surface between contact element and object surface can be corrected with the help of the diffractive optical element. It is now possible to use inexpensive materials, such as plastics, or simple glasses. Therefore, it is preferred, not least for economic reasons, that the contact element comprise a material having a refractive index which is greater than a refractive index of the object.

As already explained, the contact element according to the invention is particularly advantageous for ophthalmic applications. Therefore, the contact element is preferably provided as a contact glass for ophthalmic surgery with a spherical surface curvature having a diameter of between 7 and 25 mm. The radius of 7.86 mm corresponds to the typical average radius of corneal curvature. If the contact element's exit surface serving as the contact surface has this radius of curvature, the cornea substantially does not deform. Although deformation of the cornea does take place at a value of 25 mm, the reduced curvature of the cornea does have a reducing effect on aberrations to be corrected.

A particularly convenient application of the contact element is in a laser processing device comprising focusing optics which are arranged preceding the contact element and which focus bundles of the laser beam in focal points located in the object, said focusing optics being provided with a dispersive lens which increases the angle of deflection and with a second diffractive optical element which gathers the bundles coming from the dispersive lens. This second diffractive optical element has a strong bundling effect and enables shifting of the principal planes by means of the precedingly arranged dispersive lens. Thus, the entrance pupil is located relative to the first lens of the focusing optics at a distance sufficient to preferably enable insertion of a splitting element: Moreover, the second element thus allows the realization of comparatively great beam deflections during scanning of the laser beam. In a particularly convenient construction, the second element is provided as a plane-parallel plate.

In combination with the second diffractive optical element, the contact element realizes a processing device having a radius of surface curvature of 10 mm, an image field with a diameter of 11 mm and a numerical aperture of the focusing optics of 0.37.

The contact element preferably serves to establish secure coupling to the laser processing device on the element's entrance side. Therefore, the contact element's entrance side oriented towards the laser processing device is conveniently formed with suitable means for secure connection to the output side of the laser processing device or of its optical system, which output (e.g. distal end) is oriented towards the object, so that a fixation which is secure with respect to the laser processing device is possible by means of a locking mechanism. For the locking mechanism, it is suitable to provide a flange surface on the contact element, for example.

On the element's output side, the contact element ensures that the surface of the object has a desired specified shape. Suitable means are provided for rigidly connecting the contact element with the object; in an ophthalmic application, a means for fixing by suction, e.g. a suction ring as known from WO 03/002008 A1 or from EP 1159986 A2, can be used.

BRIEF DESCRIPTION OF THE DRAWINGS

The invention will be explained in more detail below by way of example and with reference to the drawings, wherein.

DETAILED DESCRIPTION

Figure 1:
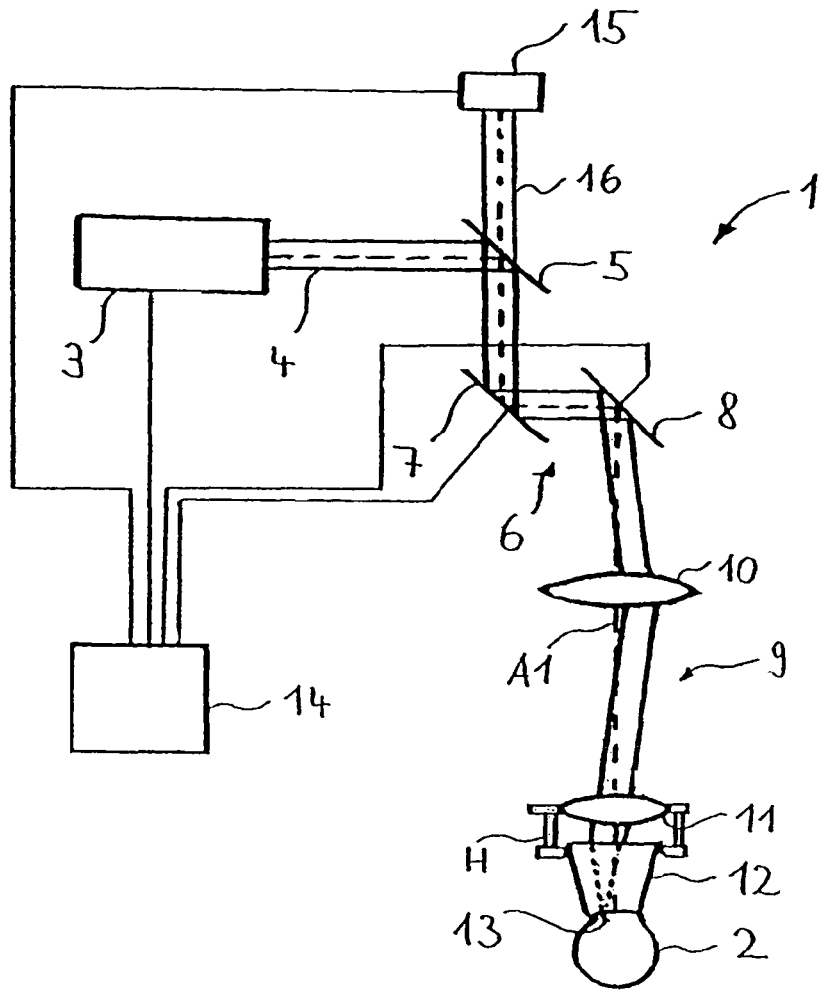
FIG. 1 shows a schematic view of a laser processing device for an ophthalmic method.

FIG. 1 shows a treatment device for an ophthalmic method similar to those described in EP 1159986 A1 and U.S. Pat. No. 5,549,632. The treatment device 1 of FIG. 1 serves to perform correction of an eyesight defect on a patient's eye 2 according to the known fs-LASIK method. For this purpose, the treatment device 1 has a laser 3 which emits pulsed laser radiation. The pulse duration is within the femtosecond range, and the laser radiation acts by means of non-linear optical effects in the cornea, as described above. The treatment beam 4 emitted by the laser 3 along an optical axis A1 is incident on a beam splitter 5 which transmits the treatment beam 4 to a scanning unit 6. The scanning unit 6 comprises two scanning mirrors 7 and 8 which are rotatable about mutually orthogonal axes such that the scanning unit 6 deflects the treatment beam 4 two-dimensionally. Adjustable projection optics 9 focus the scanned treatment beam 4 on the eye 2. The projection optics 9 comprise a lens 10 and focusing optics 11.

Arranged following the focusing optics 11 is a contact glass 12 which is connected to the focusing optics, and thus to the beam path of the treatment device 1, via a holder H. The contact glass 12, which will be explained in more detail below, contacts the cornea of the eye 2. The optical combination of the treatment device 1 with the contact glass 2 fixed thereto causes the scanned treatment beam 4 to be focused in a focus 13 located within the cornea of the eye 2. Due to the application in the cornea 17, the angles of incidence of the laser bundle increase as the field increases. While a beam incident on the optical axis A1 impinges vertically on the cornea 17, the angle of incidence is in excess of 20 degrees already at a distance of 4 mm from the optical axis A1. This results in considerable aberrations, e.g. astigmatism. The aberrations are compensated within the optical system.

Like the laser 3, the scanning unit 6 is controlled by a control device 14 via control lines (not specifically designated). The control device 14 determines the position of the focus 13 both transverse to the optical axis A1 (by the scanning mirrors 7 and 8) and in the direction of the optical axis A1 (by shifting the projection optics 9). The control device 14 further reads out a detector 15 which senses, for the purpose of measurement, radiation scattered back from the cornea and passing through the beam splitter 5 as return radiation 16.

Figure 2:
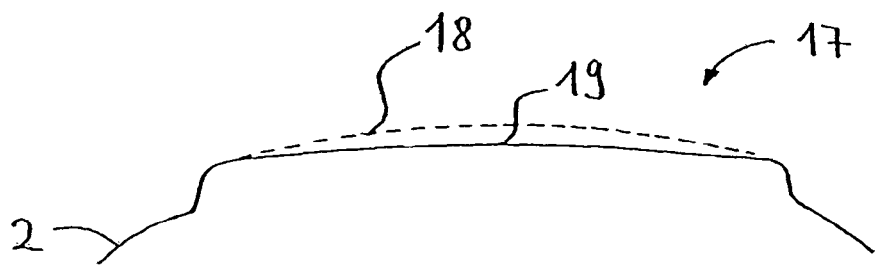
FIG. 2 shows a schematic view of a patient's cornea.

The contact glass 12 ensures that the cornea of the eye 2 obtains a desired specified shape. This is schematically illustrated in FIG. 2 which shows a sectional view of the eye's cornea 17. For exact positioning of the focus 13 in the eye's cornea 17, the curvature of the eye's cornea 17 has to be considered. The cornea 17 has an actual shape 18 which differs from patient to patient. The contact glass 12, thus, contacts the cornea 17 and deforms it to a desired specified shape 19.

The exact profile of the desired shape 19 depends on the curvature of that surface of the contact glass which faces towards the eye 2. This is evident also from FIG. 3. What is essential is that known geometrical and optical conditions for introducing and focusing the treatment beam 4 into the cornea 17 are obtained by means of the contact glass 12. Since the cornea 17 contacts the contact glass 12, which is in turn stationary with respect to the beam path of the treatment device 1 due to the holder H, an exact three-dimensional positioning of the focus 13 is achieved by controlling the scanning unit 6 as well as the adjustable projection optics 9.

Figure 3:
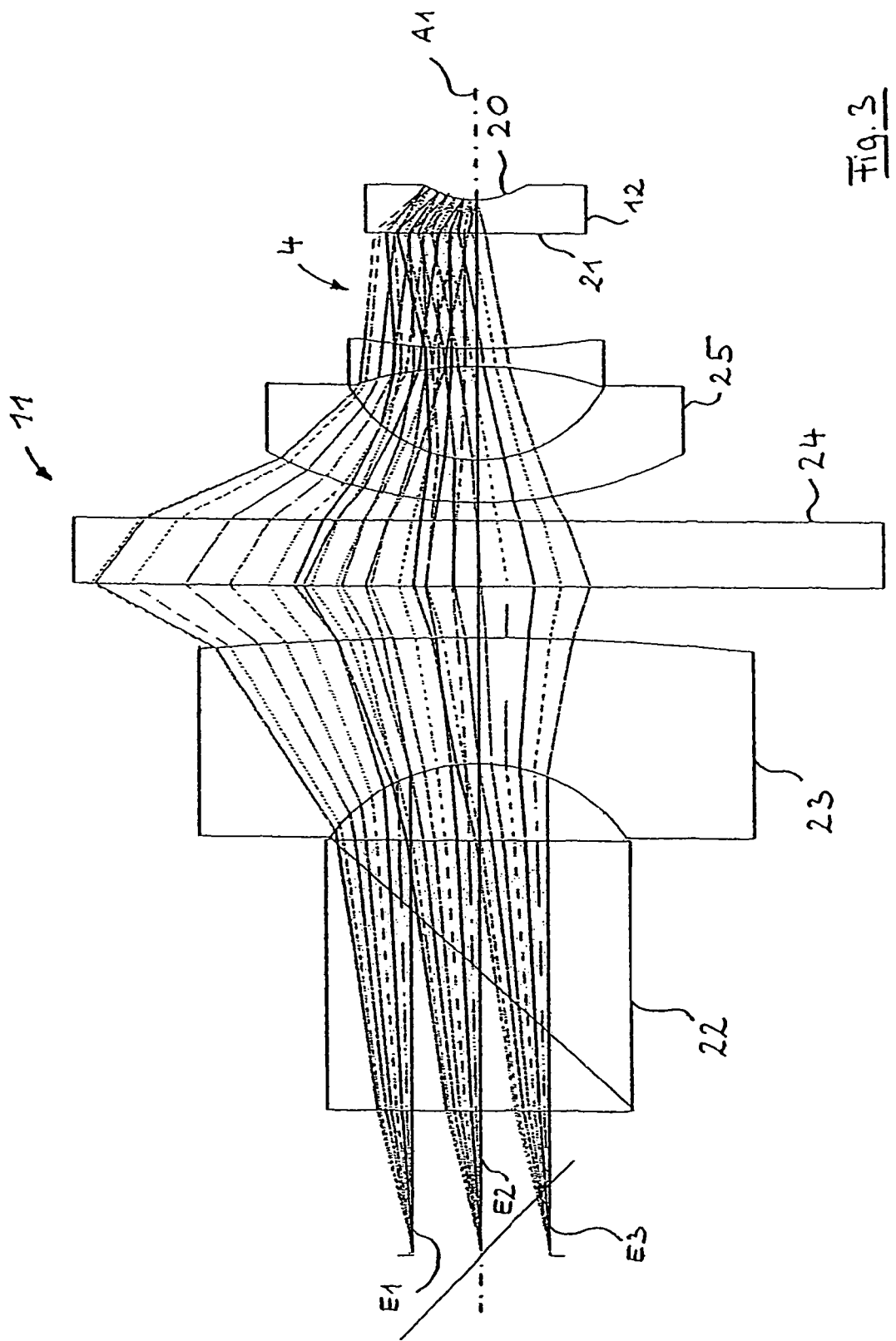
FIG. 3 shows a sectional view of focusing optics of the laser processing device of FIG. 1 including a contact glass and a beam path illustrated as an example.

FIG. 3 shows a sectional view of the focusing optics 11 comprising the contact glass 12. The contact glass 12 has a body which is transparent for the treatment beam 4. A contact surface 20 generates the desired shape 19, and the scanned treatment beam 4 is coupled in at a front surface 21 oriented to the focusing optics 11. In the described construction, the contact surface 20 is spherical and has an inner radius of 10 mm which is slightly greater than the corneal radius of the patient (e.g. 8 mm), in the exemplary embodiment. The corneal radius of the eye 2 is suitably adapted to the radius of the contact glass 12, e. g. due to the contact glass being drawn onto the eye 2 by negative pressure. As a consequence, the eye 2 is fixed by the connection thus established. Since the difference in radius between the cornea 17 in its natural state and the contact glass 12 is small, the internal pressure in the eye is not noticeably increased when adaptating the radiuses.

Further, a flange surface (not specifically shown) is formed on the contact glass 12, at which surface the contact glass 12 is fixed in the holder H (also not shown in FIG. 3 for simplification) by clamping. The flange surface constitutes a fixing means adapted to the holder H which realizes a locking mechanism.

As FIG. 3 shows, parallel bundles E1, E2 and E3 from the projection optics 9 or from the lens 10 enter the focusing optics 11. The diagram also shows several bundles for various deflections occurring during scanning. The entrance bundles E1 to E3 indicated by way of example represent a selection of field points. The bundles first pass through a beam splitter 22 which is of no further relevance to the function of the focusing optics 11. The entrance pupil of the optical construction, which pupil is arranged comparatively far at the front, enables accommodation, for example, of the beam splitter 22 as an additional coupling site. After the beam splitter 22 the ray bundles are incident on a dispersive lens 23 which, together with a subsequently arranged diffractive optical element provided as a plane-parallel plate 24, causes unusually great beam deflections which are magnified in relation to the beam deflection caused by the scanning mirrors 7, 8. A subsequent front lens group 25 directs the ray bundles onto the front surface 21 of the contact glass 12 which causes deflection onto the contact surface 20 such that rays which are incident at a distance from the optical axis A1 are diffracted towards the optical axis A1.

Figure 4:
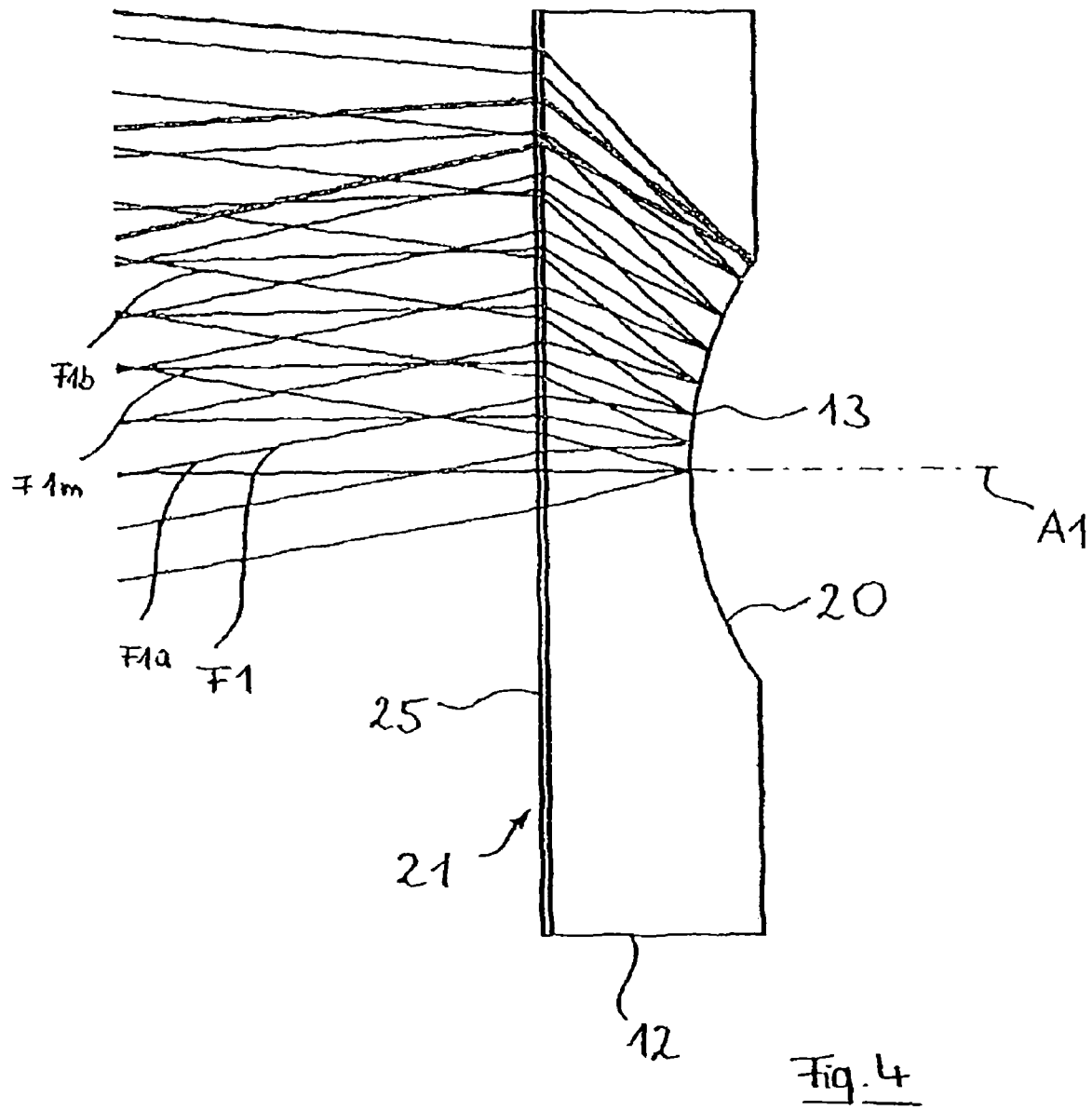
FIG. 4 shows a sectional view of the contact glass of FIG. 3.

This effect of the contact glass 12 is shown in magnified form in FIG. 4 which shows a detail of the beam path of FIG. 3 in the vicinity of the contact glass 12. Beam diffraction at the front surface 21 of the contact glass 12 is caused by a diffractive optical element 25 which, in the exemplary embodiment, is mounted to the front surface 21 and is provided as a grating structure according to the above-mentioned equations.

A focused ray bundle $\mu$l, illustrated in FIG. 4 by way of example and comprising peripheral rays F1$a$ and F1$b$ as well as a central ray F1$m$, is diffracted towards the spherical contact surface 20 by the diffractive optical element 25 such that the central ray F1$m$ impinges substantially vertically on the sphere of the contact surface 20.

On the whole, a high aperture of, for example, 0.37 is achieved on the image side in spite of relatively small angles of incidence on the diffractive optical element 25. At the same time, easier optical correction is achieved with respect to aberrations appearing in the system.

An exemplary embodiment of the diffractive optical element 25 uses the following parameters in the above-mentioned equations for determining the radial phase dependence or frequency dependence, respectively:

c1: −1.3587E-02
c2: 8.2357E-05
c3: −7.5017E-07
c4: 2.8305E-08
c5: −4.6727E-10
c6: −2.0104E-12
c7: 1.7144E-13
c8: −1.6035E-15

The image field diameter of the image field (cornea 17) curved with a radius of 10 mm is 11 mm. This is achieved by height-dependent adaptation of the number of lines (frequency) in the grating of the diffractive optical element 25. At the same time, the number of surfaces having a refractive effect is minimized in the system. Arranging the diffractive optical element 25 at the front surface 21 of the contact glass 12 enables a particularly compact structure.

The invention claimed is:

1. An optical contact element for coupling a laser processing device to an object to be processed, wherein
the laser processing device focuses a scanned laser beam through a surface of the object into a certain region of the object and
the contact element comprises a plano-concave base body a concave surface of which provides an exit side and a planar surface of which provides an entrance side, and a diffractive optical element being formed on or at a surface of the entrance side, the exit side imparting a defined surface curvature to the surface of the object upon contact therewith, wherein
the entrance side cross section is larger than a cross section of the scanned laser beam which is scanned over the entrance side, and
the diffractive optical element being configured to reduce the angle of incidence of the laser radiation on an interface between the surface of the object and the exit side of the contact element peripheral to an optical axis, the angle of incidence being measured from a normal to the defined surface curvature on the surface of the object across the exit side that imparts the defined surface curvature to the surface of the object.

2. The contact element as claimed in claim 1, wherein the defined surface curvature is substantially rotation-symmetrical to an optical axis of the laser processing device.

3. The contact element as claimed in claim 2, wherein the diffractive optical element diffracts laser radiation incident at a distance from the optical axis towards the optical axis, with the angle of diffraction increasing as a distance from the optical axis increases.

4. The contact element as claimed in claim 3, wherein the diffractive optical element comprises a grating structure having a number of grating lines depending on the distance from the optical axis.

5. The contact element as claimed in claim 4, wherein a line number of the grating is at least 220 lines per millimeter and not above 500 lines per millimeter.

6. The contact element as claimed in claim 2, wherein the contact element comprises a contact glass for ophthalmic surgery with the exit side having a substantially spherical surface curvature with a radius of between about seven and about twenty five millimeters.

7. The contact element as claimed in claim 1, wherein the contact element comprises a material whose refractive index is greater than a refractive index of the object.

8. A laser processing device comprising:
a laser emitting laser radiation and a scanning unit deflecting the laser radiation by an angle of deflection to provide scanned laser radiation;
a contact element including a plano-concave base body a concave surface of which provides an exit side, a planar surface of which provides an entrance side, wherein a diffractive optical element is formed on or at a surface of the entrance side, the exit side imparting a defined surface curvature to the surface of an object upon contact therewith, wherein the entrance side cross section is larger than a cross section of the scanned laser radiation which is deflected by the scanning unit over the entrance side;
wherein the diffractive optical element is configured to reduce the angle of incidence of the scanned laser radiation on an interface between the surface of the object and the exit side of the contact element peripheral to an optical axis, the angle of incidence being measured from a normal to the defined surface curvature on the surface of the object across the exit side that imparts the defined surface curvature to the surface of the object; focusing optics arranged preceding the contact element, said focusing optics focusing the scanned laser radiation into focal points located in the object; wherein the focusing optics comprise a dispersive lens increasing the angle of deflection and a second diffractive optical element gathering the bundles coming from the dispersive lens.

9. The laser processing device as claimed in claim 8, wherein the second diffractive optical element is provided on a plane-parallel plate.

10. The laser processing device as claimed in claim 8, wherein the exit side of the contact element has a radius of surface curvature of about ten millimeters, an image field that has a diameter of about eleven millimeters, and a numerical aperture of the focusing optics that is about 0.37.

11. A laser processing device comprising:
means for generating scanned laser radiation;
a contact element including a plano-concave body a concave surface of which provides an exit side and a planar surface of which provides an entrance side, the exit side imparting a defined surface curvature to the surface of an object upon contact therewith;
means for diffractive reduction of an angle of incidence of the laser radiation on an interface between the surface of the object and the exit side of the contact element peripheral to an optical axis, the angle of incidence being measured from a normal to the defined surface curvature on the surface of the object across the exit side that imparts the defined surface curvature to the surface of the object;
means for focusing bundles of the laser radiation into focal points located in the object; wherein the means for focusing comprises means for increasing the angle of deflection and means for diffractive gathering of the bundles coming from the means for increasing the angle of deflection; and
wherein the means for generating scanned laser radiation scans the scanned laser radiation over the means for diffractive gathering.

12. The laser processing device as claimed in claim 11, wherein means for diffractive gathering is provided on a plane-parallel plate.

13. The laser processing device as claimed in claim 11, wherein the means for imparting a defined surface curvature has a radius of surface curvature of about ten millimeters, an image field has a diameter of about eleven millimeters, and a numerical aperture of the means for focusing about 0.37.

* * * * *